United States Patent

Ciacca

[11] Patent Number: 5,228,458
[45] Date of Patent: Jul. 20, 1993

[54] RELAXATION METHOD FOR THE TREATMENT OF CONTRACTURES OF THE PARAVERTEBRAL MUSCLES

[75] Inventor: Giulio Ciacca, Perugiq, Italy

[73] Assignee: Giontella Massimo, Florence, Italy

[21] Appl. No.: 691,641

[22] Filed: Mar. 27, 1991

[30] Foreign Application Priority Data

Apr. 10, 1990 [IT] Italy .................................. 9362 A90
Oct. 4, 1990 [IT] Italy .................................. 9499 A90

[51] Int. Cl.⁵ .......................................... A61F 13/00
[52] U.S. Cl. .................................. 128/870; 128/845; 128/876; 602/19; 602/36
[58] Field of Search ............... 128/78, 82, 845, 155, 128/846, 870, 874, 875, 876; 602/19, 36, 38, 74, 903, 42, 54; 606/201, 204.35, 213

[56] References Cited

U.S. PATENT DOCUMENTS

| | | | |
|---|---|---|---|
| 1,785,831 | 12/1930 | Edmundson | 128/155 |
| 2,513,771 | 7/1950 | Williams | 606/213 |
| 2,541,487 | 2/1951 | Triplett | 128/78 |
| 2,730,096 | 1/1956 | Pease | 128/78 |
| 2,733,712 | 2/1956 | Wuesthoff | 128/78 |
| 3,989,039 | 11/1976 | Tunney | 606/204.35 |
| 4,732,146 | 3/1988 | Fasline et al. | 128/155 |
| 4,976,726 | 12/1990 | Haverstock | 606/213 X |
| 4,995,383 | 2/1991 | Andersson | 602/19 |
| 5,007,413 | 4/1991 | Aalvikthune | 128/870 X |

FOREIGN PATENT DOCUMENTS

| | | | |
|---|---|---|---|
| 372145 | 5/1932 | United Kingdom | 128/78 |
| 9011744 | 10/1990 | World Int. Prop. O. | 128/155 |

OTHER PUBLICATIONS

Appliances for the Spine and Trunk pp. 212 and 216, undated.

Primary Examiner—Robert A. Hafer
Assistant Examiner—Sam Rimell
Attorney, Agent, or Firm—McGlew & Tuttle

[57] ABSTRACT

To produce relaxation of paravertebral muscles exhibiting contracture a relaxation device is used having several principal horizontal parallel strips (1) of adhesive tape that are joined together in pairs by several secondary or traction vertical parallel strips (2) of adhesive tape. The self-adhesive side of the principal and secondary strips (1,2) is protected by a removable sheet of siliconized paper (4). The vertical strips (2) are designed to be fixed to the patient's back in equal numbers on either side of the spinous processes and in line with the subjacent paravertebral muscles exhibiting contracture and said horizontal strips (1) being designed to ensure correct anchorage of the device to the patient's trunk.

1 Claim, 2 Drawing Sheets

FIG. 1
FIG. 2
FIG. 3
FIG. 4
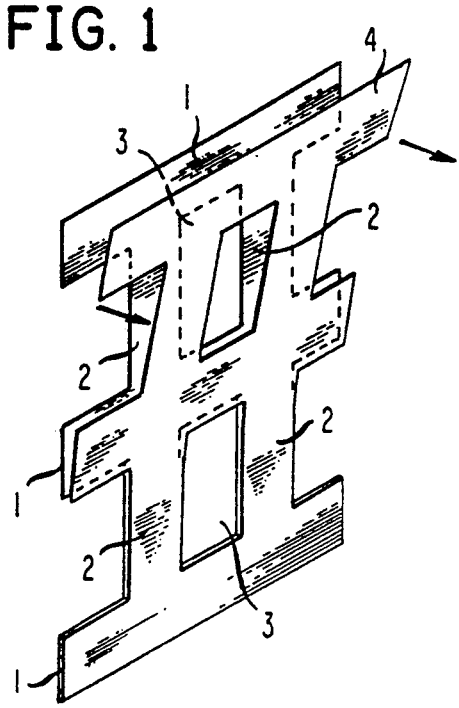
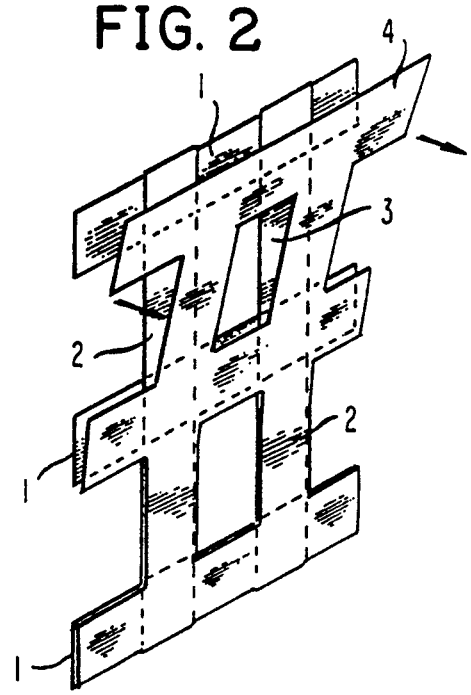
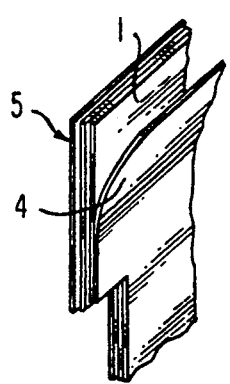
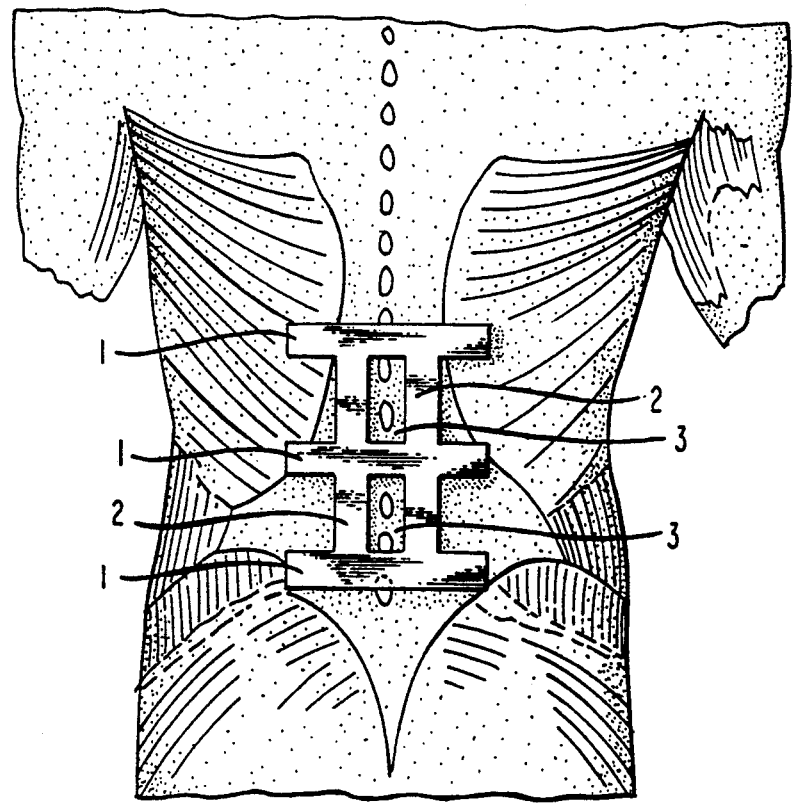

RELAXATION METHOD FOR THE TREATMENT OF CONTRACTURES OF THE PARAVERTEBRAL MUSCLES

FIELD OF THE INVENTION

The present invention relates to relaxation device for the treatment of contractures of the paravertebral muscles.

BACKGROUND OF THE INVENTION

It is known that the function of the paravertebral muscles is to support the vertebral column and enable it to be flexed and extended and make other movements. In a number of pathological conditions affecting the structures of the spine, such as discopathy, laxity of the intervertebral joints, inflammation of the ligaments, etc., there is very often a locking of the spinal structures with pain-avoiding contracture of the paravertebral muscles, which gives rise to pain-avoiding scoliosis, with the result that the spine curves permanently to one side and the patient is no longer able to straighten up.

This pain-avoiding contracture can produce pain that is even more severe than that induced by its cause and so gives rise to a vicious circle of exacerbation.

It is well known that producing relaxation of the muscles affected by contracture can eliminate the clinical symptoms in many cases. In other cases it will make possible specific physiotherapy, vertebral manipulation or the application of a corset. These are all measures that the patient can scarcely tolerate during the acute phase.

SUMMARY AND OBJECTS

The aim of the present invention is to propose a device for the relaxation of contractures of the paravertebral muscles that is particularly suitable for the treatment of the acute phase of low back pain and sciatica.

This result is achieved, according to the invention, with a relaxation device comprising at least two horizontal parallel strips of adhesive tape that are joined together by at least two transverse vertical strips of the same adhesive tape. The vertical strips are designed to adhere to the patient's back on either side of the spinous processes and in line with the subjacent paravertebral muscles exhibiting contracture. The horizontal strips are designed to ensure correct anchorage of the device to the patient's trunk.

Advantageously, the adhesive side of the strips, i.e. the side designed to adhere to the patient's skin, is protected by a sheet of siliconized paper that must be removed before the device is applied.

The main advantages of the invention are that it enables the paravertebral muscles to be relaxed, thereby producing an immediate improvement in the pain symptoms. A relaxation device according to the invention is simple to produce and can be applied quickly and easily even by paramedical staff. It is comfortable to wear and well tolerated by patients of all ages and any physical constitution and it has no contraindications.

These and further advantages and features of the invention will be better understood by any expert in the field from the description that follows and from the attached drawings, which are given by way of a practical example of the invention but do not limit its scope, and in which:

BRIEF DESCRIPTION OF THE DRAWINGS

FIG. 1 shows an overall axonometric view of a muscle relaxation device according to an initial embodiment of the invention before use;

FIG. 2 shows a relaxation device according to a further embodiment of the invention;

FIG. 3 shows a detail of the relaxation device in FIG. 1;

FIG. 4 shows the relaxation device in FIG. 1 after application to the region of the erector muscle of the vertebral column;

DETAILED DESCRIPTION OF THE PREFERRED EMBODIMENT

Figure 5:
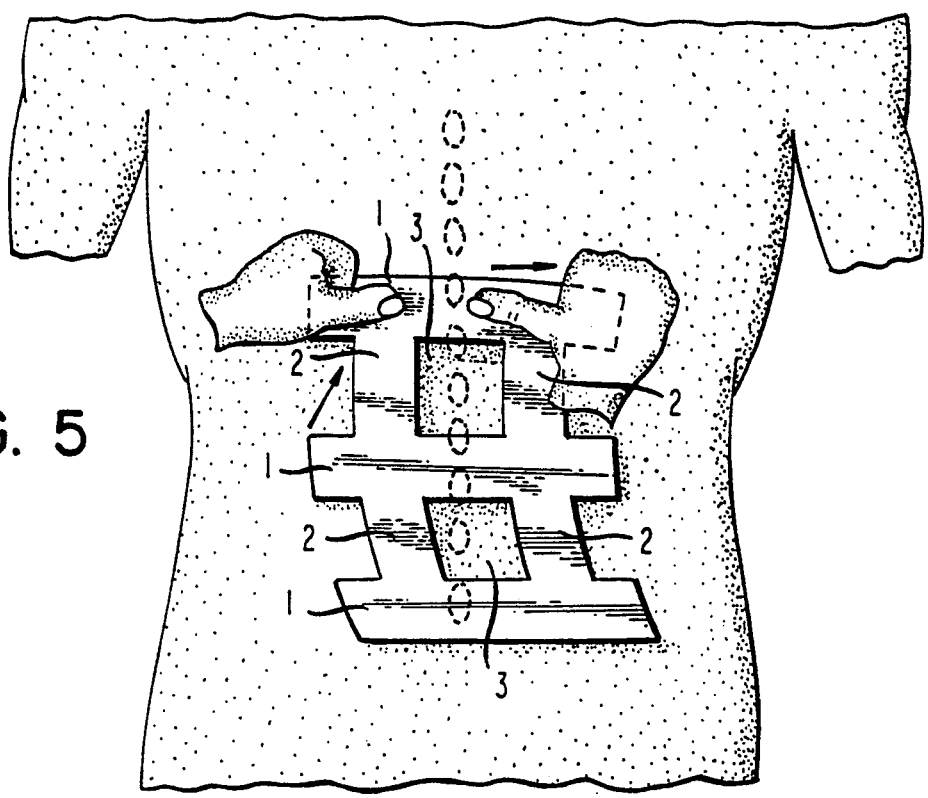
FIG. 5 illustrates the way to commence application of the relaxation device to the patient's back.

Reduced to its basic structure and with reference to FIGS. 1 and 3 in the attached drawings, a relaxation device for the treatment of contracture of the paravertebral muscles according to the invention comprises three principal horizontal parallel strips 1 of adhesive tape of ample width (e.g. 40-50 mm) and approximately 20-25 cm in length that are joined together in pairs to form a single unit by two secondary of traction vertical parallel strips 2 of the same adhesive tape of the same width as the principal strips and approximately 4-6 cm in length in such a way that between each pair of horizontal strips 1 there is a median zone 3 free of adhesive fabric measuring approximately 2-3 cm × 5-6 cm and that the two ends of the horizontal strips 1 extend beyond the two vertical strips 2 by approximately 3-5 cm.

All the strips 1,2 can be made in a single piece by being stamped out of a piece of non-elastic fabric with a self-adhesive side of the type used for plasters.

To increase the strength of the relaxation device there is provision, according to the invention, to use several pieces of non-elastic, self-adhesive fabric laid one on top of the other and then stamped out.

The complanation between the horizontal strips 1 and the vertical strips 2 of the relaxation device makes manual application of the device very simple and anchorage to the patient's back highly efficient.

To increase the rigidity of the relaxation device there is provision, according to the invention, to attach to the dorsal, i.e. non-adhesive, side of the device a plate 5 of adhesive felt or plastic material. This being fixed to the back of the piece of fabric before it is stamped out.

The sheet 4 of siliconized paper that protects the adhesive side of the strips 1,2 and has to be removed at the time the device is applied. This sheet is preferably divided longitudinally or transversely in two pieces. This being all the more advantageous the longer the strips 1,2 are.

In certain cases it may be useful, in order to achieve a more effective vertical relaxing effect, for the two vertical strips 2 to be joined together by two horizontal strips 1, only at their upper and lower ends, so as to leave uncovered by adhesive fabric a single median zone 3.

With reference to FIG. 2 in the attached drawings the horizontal strips 1 are laid on top of the vertical strips 2 on the non-adhesive side of the latter and joined together by sewing.

The relaxation device is applied as follows.

Figure 6:
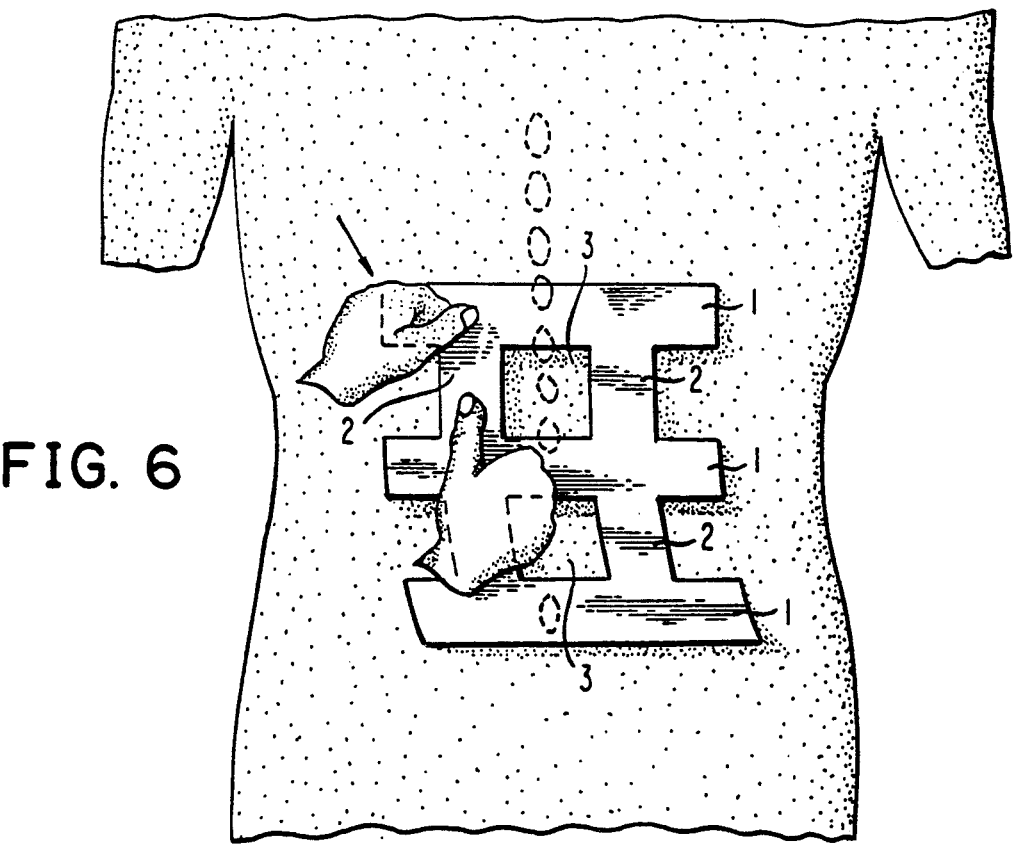
FIG. 6 illustrates the way to continue application of the relaxation device.

After the segment of siliconized paper 4 covering the upper horizontal adhesive strip 1 has been removed, the strip is fixed to the patient's back in line with the zone of dorsolumbar passage. The strip is applied with transverse pressure being exerted with the thumb of one or both hands (see FIG. 5). Then, after the siliconized paper 4 has been removed from the portion of one of the vertical adhesive strips 2, that portion or the strip 2 is applied with a combination of pressure and downward traction exerted by the thumb of the right hand. At the same time the left hand presses on the upper, horizontal strip 1 already applied (see FIG. 6). In the same way, the corresponding portion of the other vertical strip 2 is applied. After that the median horizontal adhesive strip 1 is attached. The lower portions of each of the vertical adhesive strips 2 are applied with the same technique of pressure and downward traction. Finally, the lower horizontal adhesive strip 1 is applied.

With the muscle relaxation device thus applied, the paravertebral muscles exhibiting contracture, that lie beneath the two vertical adhesive strips 2, will be subject to energetic traction in the opposite direction to that of the contracture, i.e. downwards. This will happen for a period of between several hours and several days and thus giving them sufficient time to relax.

It goes without saying that the vertical adhesive strips 2 can number more than two, i.e. four or six, but in each case the two strips at the center must be a sufficient distance apart to enable them to be applied either side of the spinous processes.

In practice the execution details can, in any event, vary in an equivalent manner for the shape, dimensions, arrangement of the elements, nature of the materials used, without departing from the scope of the solution concept used and therefore remaining within the limits of protection afforded by the present patent for industrial invention.

I claim:

1. A method for relaxation of contracture of paravertebral muscles of a patient, the method comprising the steps of: affixing by adhesion a substantially non-elastic traction strip having vertical strip portions and horizontal strip portions to and substantially in-line with the paravertebral muscles of the patient, said vertical strip portions being aligned parallel with and on opposite sides of the spinous process subjecting the paravertebral muscles beneath said traction strip to energetic traction in a substantially opposite direction to the contracture; and holding the paravertebral muscles in said energetic traction with said traction strip until the paravertebral muscles relax.

* * * * *